United States Patent [19]

Darnell

[11] Patent Number: 4,968,251
[45] Date of Patent: Nov. 6, 1990

[54] TREATMENT OF A TOOTH

[76] Inventor: Daniel H. Darnell, 508 Bangor Ave., Hanceville, Ala. 35077

[21] Appl. No.: 374,985

[22] Filed: Jul. 3, 1989

[51] Int. Cl.⁵ ............................................. A61C 15/00
[52] U.S. Cl. ........................................ 433/216; 433/80
[58] Field of Search .............. 433/80, 136, 215, 217.1, 433/229, 216; 604/77; 128/861

[56] References Cited

U.S. PATENT DOCUMENTS

| | | | |
|---|---|---|---|
| 2,257,709 | 9/1941 | Anderson | 433/215 |
| 3,073,300 | 1/1963 | Berghash | 128/136 |
| 3,247,844 | 4/1966 | Berghash | 128/136 |
| 3,448,738 | 6/1969 | Berghash | 128/136 |
| 3,527,219 | 9/1970 | Greenberg | 433/215 |
| 3,624,909 | 12/1971 | Greenberg | 433/80 |
| 3,657,413 | 4/1972 | Rosenthal | 424/81 |
| 3,998,945 | 12/1976 | Vit | 424/53 |
| 4,064,628 | 12/1977 | Weitzman | 433/80 |
| 4,173,505 | 11/1979 | Jacobs | 128/861 |
| 4,302,441 | 11/1981 | Muhlemann et al. | 424/48 |
| 4,428,373 | 1/1984 | Seid et al. | 433/00 |
| 4,431,631 | 2/1984 | Clipper et al. | 424/53 |
| 4,522,805 | 6/1985 | Gordon | 424/52 |
| 4,537,778 | 8/1985 | Clipper et al. | 424/53 |
| 4,592,487 | 6/1986 | Simon et al. | 222/94 |
| 4,592,488 | 6/1986 | Simon et al. | 222/94 |
| 4,770,634 | 9/1988 | Pellico | 433/215 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |

OTHER PUBLICATIONS

Bleaching; Tetracycline Stains by Richard M. Zillich DDS, Continuing Education Article #2, vol. V, No. 6 Jun. 1984, p. 465.

Primary Examiner—Cary E. Stone
Attorney, Agent, or Firm—Frijouf, Rust & Pyle

[57] ABSTRACT

An apparatus and method is disclosed for an improvement in the treatment of a tooth or teeth. The improved method comprises the steps of making a model of the tooth and molding a stint to overlay the model of the tooth. The stint defines an internal region for receiving a retaining material therein. An active agent is inserted into the retaining material and the stint containing the retaining material and the active agent is placed upon the tooth. The improved apparatus comprises a stint having an internal region and an external region with the internal region of the stint being defined for overlaying the tooth. A retaining material is disposed within the internal region of the stint to retain the active agent for enabling the active agent to be maintained in contact with the tooth when the stint is inserted upon the tooth.

38 Claims, 4 Drawing Sheets

PRIOR ART

FIG. 1A

PRIOR ART

FIG. 1B

PRIOR ART

FIG. 1C

PRIOR ART

FIG. 1D

PRIOR ART

FIG. 1E

PRIOR ART

TREATMENT OF A TOOTH

BACKGROUND OF THE INVENTION

1. Field of the Invention

This invention relates to medicine and dentistry and more particularly to an improved method and apparatus for applying an active agent to the surface of a tooth and/or other oral structures.

2. Prior Art Statement

The prior art has known many devices and methods for externally treating a tooth or teeth of a patient. The most primitive method of externally treating a tooth involves the direct application of an active agent to the tooth of the patient. Examples of the external treatment of a tooth includes the direct application of active agents such as fluoride, tooth whiteners, antibiotics, antihistamines and topical anesthetics.

Although the external treatment of a tooth by the direct application of an active agent has achieved some success, several problems exist with this method. First, the direct application of an active agent is generally inefficient since the active agent can be applied to the surface of the tooth for only a relatively short period of time. The relatively short period of time of application is determined by the length of time the active agent remains on the tooth of the patient. The length of time the active agent remains on the tooth of the patient is generally determined by the viscosity of the active agent and the ability of the active agent to remain on the tooth as well as the ability of the patient to remain immobile during the treatment.

In an effort to overcome these problems, some in the prior art have increased the concentration of the active agent in an effort to produce satisfactory results within the limited period of time permitted by the direct application of the active agent. Unfortunately, the increase in the concentration of the active agent produces undesirable side effects for the patient.

Others in the prior art have utilized a plastic stint molded to overlay the teeth of the patient in an effort to retain a tooth whitening agent in contact with the teeth of a patient over an extended period of time. Such a method is set forth in an article entitled "Nightguard Vital Bleaching" which has been published in *Quintessence International*, Volume 20, March, 1989. In this method, a stint is molded to fit the entire upper or lower teeth of the patient and to seal with the gingiva of the patient. The active agent is introduced into the stint, and the stint is inserted upon the teeth of the patient to retain the active agent in intimate contact with the teeth of the patient.

Although the use of a plastic stint allowed the active agent to remain in contact with the teeth for an extended period of time, the use of the plastic stint had certain disadvantages. First, since the plastic stint was molded to intimately fit with the entire upper or lower teeth of the patient, the stint was uncomfortable due to the tightness of the fit with the teeth. Second, the stint sealed with the gingiva of the patient making the stint incapable of fitting with a single tooth or just several teeth, since such the stint could not properly seal with the gingiva of the patient. Third, the stint had to be cut back adjacent to the gingival margin to prevent undesired deterioration of the gingiva due to the intimate contact of the stint with the gingiva during the treatment process. Fourth, the intimate fit of the stint with the entire upper or lower teeth of the patient prevented ingress and egress of oxygen to the internal region of the stint. Fifth, the intimate fit of the stint with the entire upper or lower teeth of the patient made the stint difficult to remove in some instances. Sixth, notwithstanding the intimate fit of the stint with the entire upper or lower teeth of the patient, the active agent within the internal region of the stint would over time migrate from the stint thus reducing the effectiveness of the active agent upon the teeth.

Therefore, it is an object of the present invention to provide an improved method and apparatus for treating a tooth with an active agent which produces results which are superior to the results heretofore known to the art.

Another object of this invention is to provide an improved method and apparatus for treating a tooth with an active agent wherein a retaining means is disposed within a stint for maintaining the active agent therein.

Another object of this invention is to provide an improved method and apparatus for treating a tooth with an active agent wherein a retaining means is disposed within a stint for maintaining the active agent against the surface of the tooth of the patient.

Another object of this invention is to provide an improved method and apparatus for treating a tooth with an active agent wherein a retaining means is disposed within a stint for providing baffles for the active agent to prevent the loss of the active agent from the stint.

Another object of this invention is to provide an improved method and apparatus for treating a tooth with an active agent wherein a plastic stint is spaced apart from the surface of the tooth of the patient for allowing the patient to comply for an adequate period of time to complete the treatment by the active agent.

Another object of this invention is to provide an improved method and apparatus for treating a tooth with an active agent wherein a plastic stint is molded with a resilient retaining means interposed between the stint and the tooth of the patient to make the stint comfortable to wear for the patient.

Another object of this invention is to provide an improved method and apparatus for treating a tooth or other oral structures within the oral cavity with an active agent.

Another object of this invention is to provide an improved method and apparatus for treating a tooth with an active agent which is capable of fitting with a single tooth or a plurality of teeth of the patient.

Another object of this invention is to provide an improved method and apparatus for treating a tooth with an active agent wherein a stint may overlie the gingival margin without deterioration or irritation of the gingiva of the patient.

Another object of this invention is to provide an improved method and apparatus for treating a tooth with an active agent wherein a stint allows the ingress and egress of oxygen to the gingival tissue adjacent to the stint.

Another object of this invention is to provide an improved method and apparatus for treating a tooth with an active agent wherein a stint may be easily removed by the patient.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly other objects and a full understanding of the invention may be had by referring to the summary of the invention, the detailed description describing the preferred embodiment, in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved method of treating a tooth with an active agent, comprising the steps of making a model of the tooth and molding a stint to define an internal region for receiving a retaining material to overlay the tooth. An active agent is introduced onto the retaining material, and the stint containing the retaining material and the active agent is applied upon the tooth.

In a more specific embodiment of the invention, the stint is vacuum formed from a sheet of plastic material over the model of the tooth. In one embodiment, the stint is vacuum formed from a sheet of plastic material with a retaining material interposed between the sheet of plastic material and the model of the tooth. Preferably, the stint is trimmed to terminate at the juncture of the tooth and the gingival tissue.

The retaining material is secured within the internal region of the stint by friction, adhesives or by heat fusion. The retaining material may be inserted into the internal region of the stint during the molding of the stint or subsequent to the formation of the stint. The retaining material may be either a non-absorbent retaining material or an absorbent retaining material.

In one embodiment of the present invention, the retaining material may be preferentially inserted into selected portions of the internal region of the stint to preferentially treat a portion of a tooth adjacent the retaining material.

The invention is also incorporated into an improved apparatus of treating a tooth, comprising a stint having an internal region and an external region with the internal region of the stint defined for overlaying the tooth. The stint terminates at the juncture of the tooth and the gingival tissue. A retaining material is secured within the internal region of the stint with the retaining material terminating at the termination of the stint adjacent to the juncture of the tooth and the gingival tissue. The retaining material retains the active agent therein enabling the active agent to be maintained in contact with the tooth when the stint containing the retaining material and the active agent is applied upon the tooth.

The foregoing has outlined rather broadly the more pertinent and important features of the present invention in order that the detailed description that follows may be better understood so that the present contribution to the art can be more fully appreciated. Additional features of the invention which form the subject of the claims of the invention will be described hereinafter. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIGS. 1A-1F are rear views partially in section of the prior art process of treating a tooth with a stint with FIGS. 1A-1F illustrating the individual process steps;

FIGS. 2A-2F are rear views partially in section of a first embodiment of the present invention for treating a tooth with a stint with FIGS. 2A-2F illustrating the individual process steps;

FIG. 3A-3H are rear views partially in section of a second embodiment of the present invention for treating a tooth with a stint with FIGS. 3A-3H illustrating the individual process steps;

Similar reference characters refer to similar parts throughout the several Figures of the drawings.

DETAILED DISCUSSION

Figure 1A:
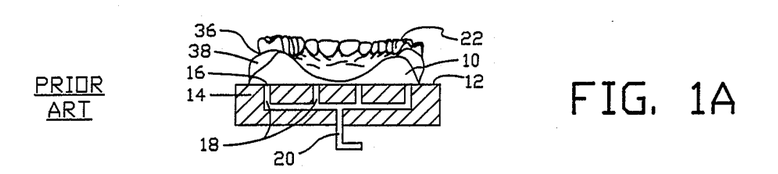
FIG. 1A is a first step in the prior art process illustrating the positioning of a model of the teeth upon a vacuum table.

FIGS. 1A-1F illustrate a method of whitening a tooth with an active agent in accordance with the teaching of the prior art such as the prior art article "Nightguard Vital Bleaching" (*Quintessence International*, Volume 20, March, 1989). FIG. 1A is a first step in the prior art process illustrating the positioning of a model 10 upon an upper surface 12 of a vacuum table 14. The vacuum table 14 defines a plurality of apertures 16 which are connected by conduits 18 to a manifold 20. The manifold 20 is connected to a source of vacuum (not shown). A model 10 is a reproduction of the teeth 22 of a patient and is constructed in a conventional manner as should be well known to those skilled in the art. The model 10 is positioned upon the upper surface 12 of the vacuum table 14 as shown.

Figure 1B:
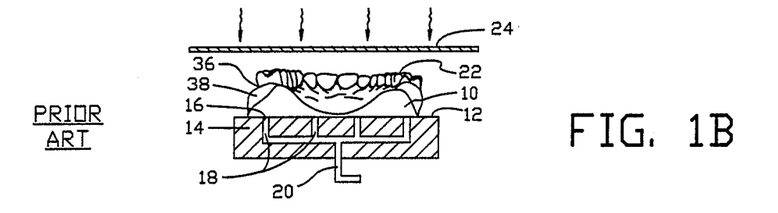
FIG. 1B is a second step in the prior art process illustrating the heating of a plastic material for forming the stint.

FIG. 1B is a second step in the prior art process illustrating the heating of a sheet plastic material 24 for forming a stint 30.

Figure 1C:
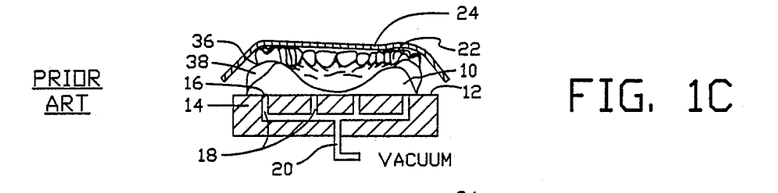
FIG. 1C is a third step in the prior art process illustrating the positioning of the heated plastic material upon the model.

FIG. 1C is a third step in the prior art process illustrating the positioning of the heated sheet of plastic material 24 upon the model 10. The heated sheet of plastic material 24 begins to form into the contour of the model 10 by the action of gravity.

Figure 1D:
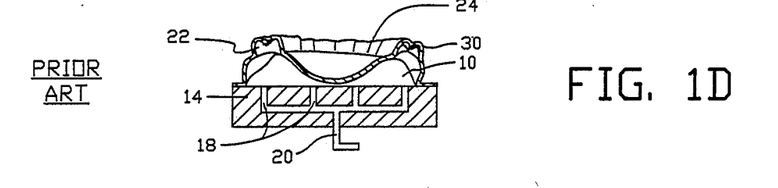
FIG. 1D is a fourth step in the prior art process illustrating the vacuum forming of the heated plastic material upon the model to form the stint.

FIG. 1D is a fourth step in the prior art process illustrating the application of a vacuum to the manifold 20 for vacuum forming of the heated plastic material 24 upon the model 10 to form the stint 30. The vacuum forming process forms the heated plastic material 24 into an exact reproduction of the outer surfaces of the teeth 22 of the patient.

Figure 1E:
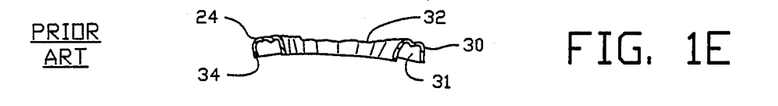
FIG. 1E is a fifth step in the prior art process illustrating the removal of the vacuum formed stint from the model and the trimming of the vacuum formed stint.

FIG. 1E is a fifth step in the prior art process illustrating the removal of the stint 30 from the model 10. The stint 30 is formed with an internal region 31 and an external region 32. The stint 30 is trimmed by a cutting tool (not shown) such as crown scissors to terminate at 34 proximate the junction 36 of the teeth 22 and the gingival tissue 38 commonly referred to as the tooth gingival margin.

Figure 1F:
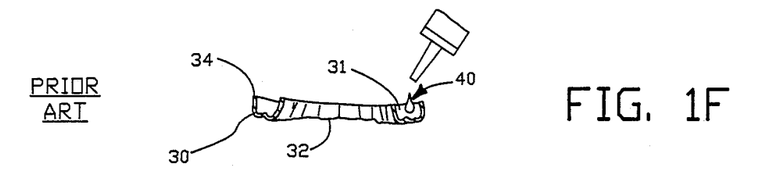
FIG. 1F is a seventh step in the prior art process illustrating the introduction of the active agent within the stint.

FIG. 1F is a seventh step in the prior art process illustrating the introduction of the active agent 40 within the internal region 31 of the stint 30. The prior art has used this process for whitening teeth through the use of a nonaqueous oral peroxy compound as an active agent. After the active agent is applied, the stint 30 containing the active agent 40 is applied upon the teeth 22 of the patient. The termination 34 of the stint 30 seals with the gingiva 38 to retain the active agent 40 within the internal region 31 of the stint 30.

Figure 2A:
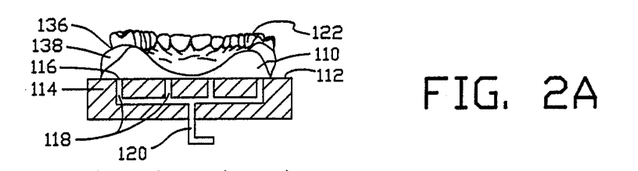
FIG. 2A is a first step in the first embodiment of the present invention illustrating the positioning of a model of the teeth upon a vacuum table.

FIGS. 2A-2F are rear views partially in section of a first embodiment of the present invention for treating a tooth with a stint and with FIGS. 2A-2F illustrating the individual process steps. FIG. 2A is a first step in the first embodiment of the present invention illustrating the positioning of a model 110 upon an upper surface 112 of a vacuum table 114. The vacuum table 114 defines a plurality of apertures 116 which are connected by conduits 118 to a manifold 120 for connection to a source of vacuum (not shown). A model 110 is a reproduction of the teeth 122 of a patient and is constructed in a conventional manner. The model 110 is positioned upon the upper surface 112 of the vacuum table 114 as shown.

In contrast to the prior art process shown in FIGS. 1A-1F. a retaining material 126 is positioned upon the model 110. The retaining material in this embodiment is shown as a close cell foam material such as low density foamed polyethylene having a thickness of 1/32" to 3/32". The retaining material 126 possesses a natural resiliency as well as non uniform outer surfaces which are desirable for the practice of the present invention.

Figure 2B:
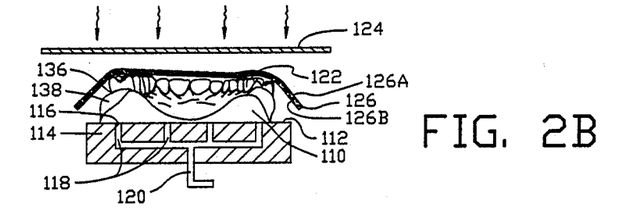
FIG. 2B is a second step in the first embodiment of the present invention illustrating a sheet of a retaining material positioned upon the model of the teeth and the heating of a plastic material for forming the stint.

FIG. 2B is a second step in the first embodiment of the present invention illustrating the heating of a plastic material 124 for forming the stint 130. The plastic material 124 for the stint 130 is selected to be easily formed at moderate temperatures such as 0.020 inch thickness polycarbonate. Preferably, the melting temperature of the retaining material 126 is less than the melting temperature of the plastic material 124 for the stint 130.

Figure 2C:
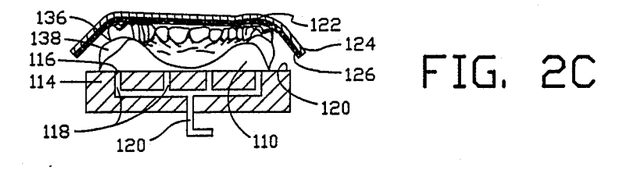
FIG. 2C is a third step in the first embodiment of the present invention illustrating the positioning of the heated plastic material upon the model with the retaining material interposed therebetween.

FIG. 2C is a third step in the first embodiment of the present invention illustrating the positioning of the heated sheet of plastic material 124 upon an inner surface 126A of the retaining material 126 while the retaining material 126 rests on the model 110. Since the melting temperature of the retaining material 126 is less than the melting temperature of the plastic material 124, the inner surface 126A of the retaining material 126 is heat fused to the plastic material 124.

Preferably, the melting temperature of the plastic material 124 for the stint 130 is selected to be higher than the melting temperature of the retaining material 126 to enable heat fusion of the inner surface 126A while being sufficiently low to prevent the destruction, melting or distortion of the interior or an outer surface 126B of the retaining material 126. Furthermore, only the inner surface 126A of the retaining material 126 is heat fused to the plastic material 124 for maintaining the resiliency of the resilient material 126.

After the heated sheet of plastic material 124 fuses with the retaining material 126, the sheet of plastic material 124 and the fused retaining material 126 begin to form into the contour of the model 110 by the action of gravity.

Figure 2D:
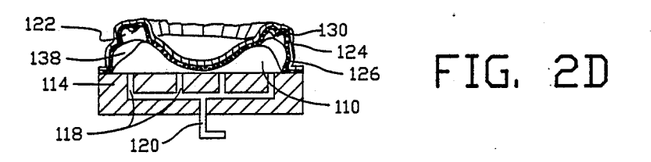
FIG. 2D is a fourth step in the first embodiment of the present invention illustrating the vacuum forming of the heated plastic material and the retaining material upon the model to form the stint.

FIG. 2D is a fourth step in the first embodiment of the present invention illustrating the application of a vacuum to the manifold 120 for vacuum forming of the heated plastic material 124 and the interposed retaining material 126 upon the model 110 to form the stint 130. The vacuum forming process forms the heated plastic material 124 into a reproduction of the outer surfaces of the teeth 122 of the patient. However, in contrast to the prior art process, the internal region of the stint 130 is spaced from the outer surfaces of the teeth 122 of the patient by the thickness of the retaining material 126.

Figure 2E:
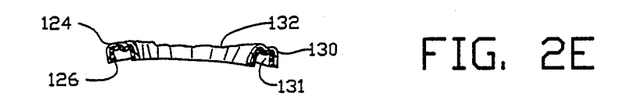
FIG. 2E is a fifth step in the first embodiment of the present invention illustrating the removal of the vacuum formed stint from the model and the trimming of the vacuum formed stint and the retaining material.

FIG. 2E is a fifth step in the first embodiment of the present invention illustrating the removal of the stint 130 from the model 110. The stint 130 is formed with an internal region 131 now defined by the retaining material 126 and an external region 132. The stint 130 is trimmed by a cutting tool (not shown) to terminate at 134 proximate the junction 136 of the teeth 122 and the gingiva tissue 138. As the stint 130 is trimmed, both the plastic material 124 and the retaining material 126 are simultaneously trimmed b the cutting tool.

Figure 2F:
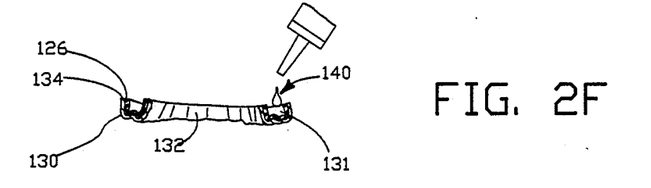
FIG. 2F is a sixth step in the first embodiment of the present invention illustrating the introduction of the active agent and the retaining material within the stint.

FIG. 2F is a sixth step in the first embodiment of the present invention illustrating the introduction of the active agent 140 within the internal region 131 of the stint 130. Preferably, the internal region 131 of the stint 130 is at least partially filled with the active agent 140 to be retained by the retaining material 126 and to provide excess quantities of the active agent 140. The presence of the retaining material 126 in the internal region 131 of the stint 130 aids in retaining the active agent 140 within the stint 130 and in close proximity to the teeth 122 of the patient to provide superior results relative to the prior art.

After the active agent 140 is introduced into the internal region 131 of the stint 130, the stint 130 is inserted over the teeth 122 of the patient. The non uniform surface of the retaining material 126 within the stint 130 provides baffles to retain the active agent 140 within the internal region 131 of the stint 130.

Figure 3A:
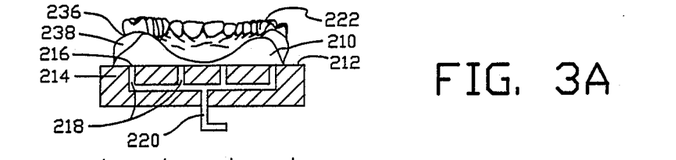
FIG. 3A is a first step in the second embodiment of the present invention illustrating the positioning of a model of the teeth upon a vacuum table.

FIGS. 3A–3I are rear views partially in section of a second embodiment of the present invention for treating a tooth with a stint with FIGS. 3A–3I illustrating the individual process steps FIG. 3A is a first step in the second embodiment of the present invention illustrating the positioning of a model 210 of the teeth 222 of a patient upon an upper surface 212 of a vacuum table 214 with the vacuum table 214 defining a plurality of apertures 216 which are connected by conduits 218 to a manifold 220 for connection to a source of vacuum (not shown).

Figure 3B:
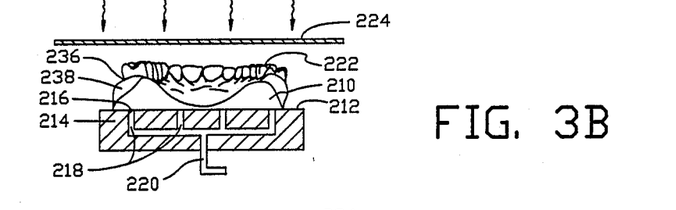
FIG. 3B is a second step in the second embodiment of the present invention illustrating the heating of a plastic material for forming the stint.

FIG. 3B is a second step in the second embodiment of the present invention illustrating the heating of a plastic material 224 for forming a stint 230 The plastic material 224 is again selected to be easily formed at moderate temperatures by conventional means.

Figure 3C:
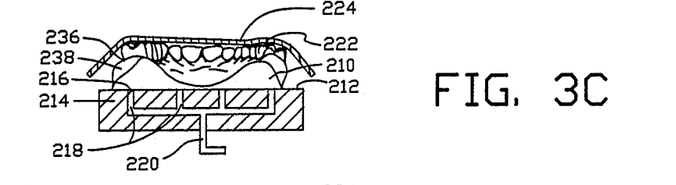
FIG. 3C is a third step in the second embodiment of the present invention illustrating the positioning of the heated plastic material upon the model.

FIG. 3C is a third step in the second embodiment of the present invention illustrating the positioning of the heated plastic material 224 upon the model 210 with the heated sheet of plastic material 224 beginning to form into the contour of the model 210 by the action of gravity.

Figure 3D:
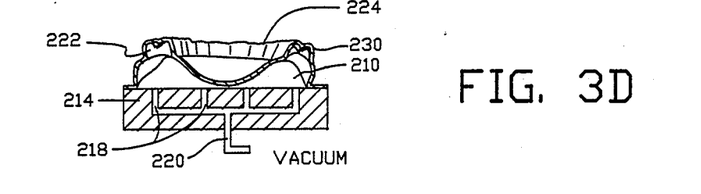
FIG. 3D is a fourth step in the second embodiment of the present invention illustrating the vacuum forming of the heated plastic material upon the model to form the stint.

FIG. 3D is a fourth step in the second embodiment of the present invention illustrating the application of a vacuum to the manifold 220 for vacuum forming of the heated plastic material 224 upon the model 210 to form the stint 230.

Figure 3E:
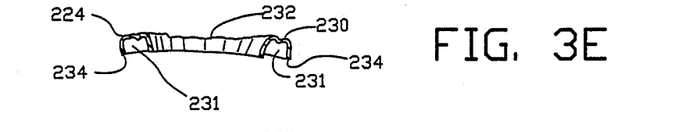
FIG. 3E is a fifth step in the second embodiment of the present invention illustrating the removal of the vacuum formed stint from the model and the trimming of the vacuum formed stint.

FIG. 3E is a fifth step in the second embodiment of the present invention illustrating the removal of the stint 230 from the model 210 with the stint 230 being formed with an internal region 231 and an external region 232. The stint 230 is trimmed by a cutting tool (not shown) to terminate at 234 proximate the junction 236 of the teeth 222 and the gingival tissue 238 commonly referred to as the tooth gingival margin.

Figure 3F:
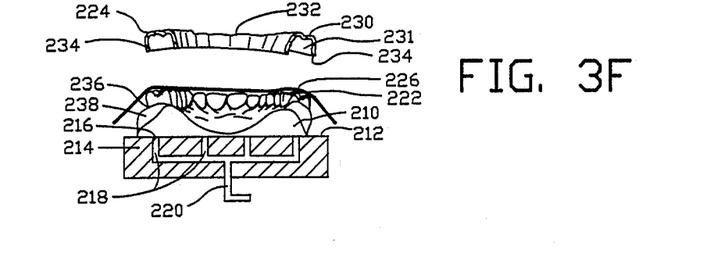
FIG. 3F is a sixth step in the second embodiment of the present invention illustrating the positioning of a retaining material upon the model.

FIG. 3F is a sixth step in the second embodiment of the present invention illustrating the positioning of a retaining material 226 upon the model 210. In this embodiment, the retaining material 226 is shown as a thin sheet of fibrous absorbent retaining material. Preferably, the fibrous absorbent retaining material 226 has a thickness of 0.001" to 0.005". The retaining material 226 may be optionally moistened for facilitating the formation thereof as will be described hereinafter.

Figure 3G:
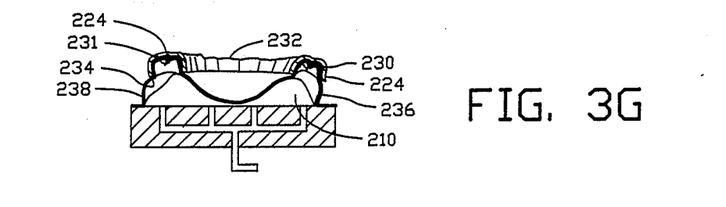
FIG. 3G is a seventh step in the second embodiment of the present invention illustrating the forming of the retaining material upon the model by the formed stint.

FIG. 3G is a seventh step in the second embodiment of the present invention illustrating the forming of the retaining material 226 upon the model 210 by the stint 230. The formed stint 230 is placed upon the model 210 with the retaining material 226 interposed therebetween. The formed stint 230 and the model 210 form the retaining material into the shape of the internal region 231. The retaining material 226 is frictionally retained within the internal region 231 of the stint 230. If desired, an adhesive may be applied to the stint 230 and/or the retaining material 226 prior to placing the stint 230 upon the model 210 with the retaining material 226 interposed therebetween for permanently securing the retaining material 226 to the stint 230.

Figure 3H:
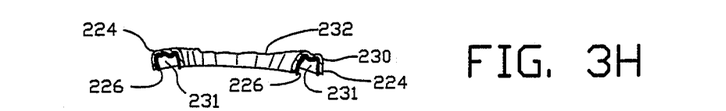
FIG. 3H is an eighth step in the second embodiment of the present invention illustrating the trimming of the retaining material to the stint.

FIG. 3H is an eighth step in the second embodiment of the present invention illustrating the trimming of the retaining material 226 to the stint 230. The retaining material 226 is trimmed by a cutting tool (not shown) adjacent the termination 234 of the stint 230.

Figure 3I:
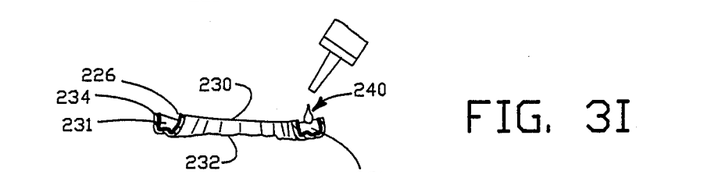
FIG. 3I is a ninth step in the second embodiment of the present invention illustrating the introduction of the active agent and the retaining material within the stint.

FIG. 3I is a ninth step in the second embodiment of the present invention illustrating the introduction of the active agent 240 within the internal region 231 of the stint 230. The presence of the absorbent retaining material 226 in the internal region 231 of the stint 230 allows the active agent 240 to be absorbed within the retaining material 226 to retain the active agent 240 in close proximity to the teeth 222 of the patient to provide superior results relative to the prior art.

Figure 4:
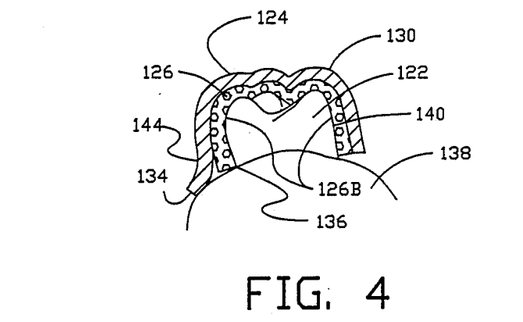
FIG. 4 is a sectional view of the improved stint shown in FIGS. 2A-2F disposed upon a tooth of a patient.

FIG. 4 is an enlarged sectional view of the first embodiment of the improved stint 130 shown in FIGS. 2A–2F containing the active agent 140 disposed upon a tooth 122 of the patient. The termination 134 of the stint 130 approximate the gingiva 138 to retain the active agent 140 within the internal region 131 of the stint 130.

In the first embodiment shown in FIG. 4. the retaining material 126 not only aids in the retention of the active agent but also allows the ingress and egress of oxygen to the gingiva tissue 138. Accordingly, the stint 130 of the present invention may utilize an overlap 144 of the gingiva tissue 138 by as much as 3.0 millimeters. The overlap 144 of the gingiva tissue 138 allowed by the stint 130 of the present invention provides a superior adaptation for treatment of the gingival tissue over the prior art stint 30. The presence of the retaining material 126 and the natural resiliency of the closed cell foam makes the stint 130 more comfortable to wear for the patient. Accordingly, the patient will be inclined to wear the stint 130 of the present invention for a longer period of time relative to the prior art stint 30 thus producing faster results relative to the prior art stint 30. Additionally, the non uniform surface of the closed cell foam enhances the retention of the active agent within the stint 130.

Figure 5:
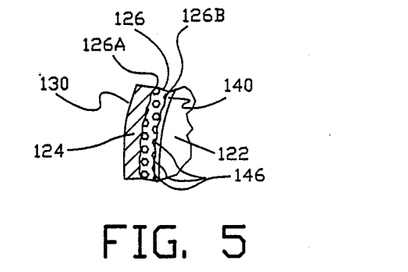
FIG. 5 is an enlarged sectional view of a portion of the improved stint shown in FIGS. 2A-2F disposed upon a tooth of a patient.

FIG. 5 is an enlarged sectional view of a portion of the improved stint 130 shown in FIG. 4. The foam retaining material 126 has a plurality of baffles or indentations 146 to trap and hold the active agent 140 against the tooth 122 to provide a superior performance relative to the prior art. Although the prior art stint 30 was closely fitted to the surface of the teeth 22, the active agent 40 within the stint 30 tended to wash out of the stint 30. In addition, areas where the prior art stint closely fitted against the surface of the tooth prevented the active agent from treating that portion of the tooth. This disadvantage of the prior art stint caused undesired irregular treatment of the tooth.

In the first embodiment of the invention, the plurality of baffles 146 of the retaining material 126 retains the active agent 140 within the stint 130 and impedes the washing away of the active agent 140 from the stint 130. Accordingly, the active agent 140 stays in contact with the surface of the teeth 122 of the patient thus providing superior results with the same active agent 140. Furthermore, the baffles 146 maintain the active agent uniformly against the surface of the tooth to provide a uniform treatment.

Figure 6:
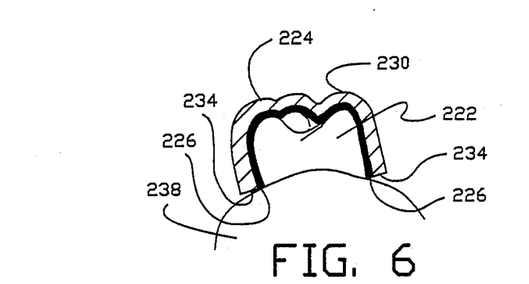
FIG. 6 is a sectional view of the improved stint shown in FIGS. 3A-3I disposed upon a tooth of a patient.

FIG. 6 is an enlarged sectional view of the second embodiment of the improved stint 230 shown in FIGS. 3A-3I disposed upon a tooth 222 of a patient. The termination 234 of the stint 230 ends with the gingiva 238 to retain the active agent 240 within the internal region 231 of the stint 230. In this example the retaining material 226 is uniformly disposed about the entire external surface of the tooth 222 of the patient.

Figure 7:
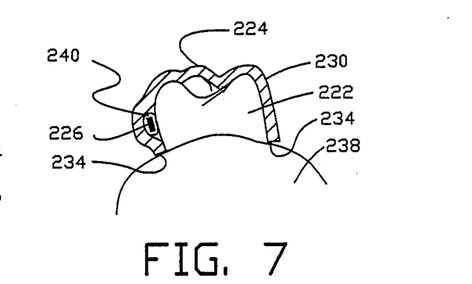
FIG. 7 is a sectional view of the improved stint shown in FIGS. 3A-3I disposed upon a tooth of a patient with the retaining material being preferentially inserted into a selected portion of the stint to preferentially treat a selected portion of the tooth.

FIG. 7 is an enlarged sectional view of the second embodiment of the improved stint 230 shown in FIGS. 3A-3I disposed upon a tooth 222 of a patient with the retaining material 226 being preferentially inserted into a selected portion of the stint 230 to preferentially treat a selected portion of the tooth 222. In some instances, only a portion of the tooth 222 requires the treatment by the active agent 240. Accordingly, the retaining material 226 may be preferentially inserted into a selected portion of the stint 230. For example, the selected portion of the tooth 222 is first identified and the retaining material 226 is temporarily affixed by means such as a temporary adhesive to the model 210 to cover the selected portion of the tooth 222. Thereafter, the stint 230 is molded in the manner shown in FIGS. 3A-3E. The retaining material 226 may then be removed from the model 210 and may be affixed by means such as a permanent adhesive to the selected portion of the stint 230. When the active agent is applied to the retaining material 226 in the selected portion of the stint 230. The retaining material 226 is in register with the selected portion of the stint 230 for preferentially treating the selected portion of the tooth 222. This advantage of the second embodiment of the improved stint enables the selective treatment of a single tooth or a selected portion or portions of a single tooth or a plurality of selected teeth.

The apparatus and method of the present invention may be utilized in various treatments of a tooth or other oral structures including the treatment for whitening teeth, fluoride treatment, as well as the application of antibiotics, antihistamines, topical anesthetics, chemotherapy, steroids, astringents, antiseptics, anti-inflammatory and the like.

In periodontal procedures such as root planing and deep scaling, the stint can be placed in the mouth of the patient to apply a topical anesthetic several minutes prior to the procedure thereby reducing the discomfort or pain to the patient. The improved stint may be used to apply a fluoride treatment for reducing post operative complications, for remineralizing the damaged areas of the root surfaces as well as insulating the surfaces to prevent sensitivity.

The improved stint of the present invention may be used in antihistamine procedures to reduce topical inflammation of periodontal structures, fluoride treatment such as the treatment of decalcification, radiation therapy and rampant caries, acute sensitive and xerostomia.

In one example, the apparatus and method of the present invention has been successfully used in a tooth whitening process. A solution of 11% perhydrol urea in a base solution of glycerine (99.9% water free) with a base stabilizer of 0.015% potassium citrate has been found to be effective as a tooth whitening agent.

The stint may be formed from a variety of materials such as polymers, copolymers, composites and the like. Stints have been successfully formed from 0.020" to 0.040" polycarbonate coping material. The polycarbonate material has been found to be more comfortable for the patient than harder material such as acrylics and the like. Furthermore, the resiliency of the polycarbonate material does not produce undesired orthodontic movement.

The foam retaining material shown in FIGS. 2A-2F may be selected from a variety of materials as should be apparent to those skilled in the art. However, superior results have been achieved using low density foam polyethylene in a thickness range of 1/32" to 3/32". In a similar manner, the fibrous retaining material shown in FIGS. 3A-3I may be selected from a variety of materials having a thickness of 0.001" to 0.005". For example, conventional filters for drip coffee makers have been found to be an effective fibrous retaining material. Other suitable materials include medical grade milioliform filter material.

The apparatus and method of the present invention when applied to a tooth whitening process has been found to produce faster results with less discomfort for the patient than the prior art process shown in FIGS. 1A-1F.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved method of treating a tooth with an active agent, comprising the steps of:

making a model of the tooth;

molding a stint to define an internal region for receiving a retaining material to overlay the tooth;

introducing the active agent into the retaining material; and applying the stint containing the retaining material and the active agent upon the tooth with the retaining material at least partially sealing the internal region from the external region of the stint proximate the termination of the stint at the juncture of the tooth and the gingiva tissue.

2. An improved method of treating a tooth with an active agent as set forth in claim 1, wherein the step of molding the stint to overlay the tooth includes vacuum forming a sheet of plastic material over the model of the tooth.

3. An improved method of treating a tooth with an active agent as set forth in claim 1, wherein the step of molding the stint to overlay the tooth includes vacuum forming a sheet of plastic material over the model of the tooth with the retaining material interposed between the sheet of plastic material and the model of the tooth.

4. An improved method of treating a tooth with an active agent as set forth in claim 1, including the step of trimming the stint to terminate at the juncture of the tooth and the gingiva tissue.

5. An improved method of treating a tooth with an active agent as set forth in claim 1, including the step of inserting the retaining material into the internal region of the stint to be frictional received therein.

6. An improved method of treating a tooth with an active agent as set forth in claim 1, including the step of inserting the retaining material into the internal region of the stint to be adhesively retained therein.

7. An improved method of treating a tooth with an active agent as set forth in claim 1, including the step of inserting the retaining material into the internal region of the stint to be heat fused to the stint.

8. An improved method of treating a tooth with an active agent as set forth in claim 1, including the step of inserting the retaining material into the internal region of the stint during the molding of the stint.

9. An improved method of treating a tooth with an active agent as set forth in claim 1, wherein the retaining material received within the internal region of the stint includes affixing a non-absorbent retaining material to the internal region of the stint.

10. An improved method of treating a tooth with an active agent as set forth in claim 1, wherein the retaining material received within the internal region of the stint includes affixing an absorbent retaining material to the internal region of the stint.

11. An improved method of treating a tooth with an active agent as set forth in claim 1, wherein the step of introducing the active agent into the retaining material includes at least partially filling the internal region of the stint with the active agent to be retained by the retaining material and to provide excess quantities of the active agent.

12. An improved method of treating a tooth with an active agent as set forth in claim 1, wherein the step of molding the stint to overlay the tooth includes molding the stint to overlay a plurality of teeth.

13. An improved method of treating a tooth with an active agent as set forth in claim 1, including the step of preferentially inserting the retaining material into selected portions of the internal region of the stint to preferentially treat a portion of the tooth adjacent the retaining material.

14. An improved method of treating a tooth with an active agent comprising the steps of:
making a model of the tooth;
molding a stint to define an internal region for receiving a retaining material to overlay the tooth;
introducing the active agent into the retaining material;
applying the stint containing the retaining material and the active agent of a bleaching agent comprising a solution of 11% perhydrol urea in a base solution of glycerine with a base stabilizer of 0.015% potassium citrate upon the tooth.

15. An improved method of whitening a tooth with an active agent, comprising the steps of:
making a model of the tooth;
molding a stint to define an internal region and an external region with the internal region overlaying the tooth and the adjacent gingiva tissue;
trimming the stint to overlay only the tooth and to terminate at the juncture of the tooth and the gingiva tissue;
inserting a sheet of retaining material into the internal region of the stint;
trimming the sheet of the retaining material to terminate at the termination of the stint;
introducing the active agent to brighten the tooth into the retaining material; and
applying the stint containing the retaining material and the active agent upon the tooth with the retaining material at least partially sealing the internal region from the external region of the stint proximate the termination of the stint at the juncture of the tooth and the gingiva tissue.

16. An improved method of treating a tooth with an active agent as set forth in claim 15, wherein the step of inserting the retaining material into the internal region of the stint includes inserting a sheet of retaining material into the internal region of the stint to be frictional received therein.

17. An improved method of treating a tooth with an active agent as set forth in claim 15, wherein the step of inserting the retaining material into the internal region of the stint includes inserting the retaining material into the internal region of the stint and adhesively fastening the retaining material to the internal region of the stint.

18. An improved method of treating a tooth with an active agent as set forth in claim 15, wherein the step of introducing the active agent into the retaining material includes at least partially filling the internal region of the stint with the active agent to provide excess quantities of the active agent.

19. An improved method of treating a tooth with an active agent as set forth in claim 15, wherein the step of molding the stint to overlay the tooth includes molding the stint to overlay a plurality of teeth.

20. An improved method of treating a tooth with an active agent as set forth in claim 15, wherein the step of inserting the retaining material into the internal region of the stint includes preferentially inserting a portion of the retaining material into the internal region of the stint to preferentially treat a portion of the tooth adjacent the portion of the retaining material.

21. An improved method of treating a tooth with an active bleaching agent, comprising the steps of:
making a model of the tooth;
molding a stint to define an internal region and an external region with the internal region overlaying the tooth and the adjacent gingiva tissue;
trimming the stint to overlay only the tooth and to terminate at the juncture of the tooth and the gingiva tissue;

inserting a sheet of retaining material into the internal region of the stint;

trimming the sheet of the retaining material to terminate at the termination of the stint;

introducing the active bleaching agent comprising a solution of 11% perhydrol urea in a base solution of glycerine with a base stabilizer of 0.015% potassium citrate to brighten the tooth into the retaining material; and applying the stint containing the retaining material and the active agent upon the tooth.

22. An improved method of whitening a tooth with an active agent, comprising the steps of:

making a model of the tooth;

positioning a retaining material between the model of the tooth and a stint material;

molding a stint from the stint material to define an internal region and an external region with the retaining material being formed adjacent to the internal region of the stint and to overlay the tooth and the adjacent gingiva tissue;

trimming the stint to overlay the tooth;

introducing the active agent to brighten the tooth into the retaining material; and applying the stint containing the retaining material and the active agent upon the tooth with the retaining material at least partially sealing the internal region from the external region of the stint proximate the termination of the stint at the juncture of the tooth and the gingiva tissue.

23. An improved method of treating a tooth with an active agent as set forth in claim 22, wherein the step of trimming the stint includes trimming the retaining material to terminate at the termination of the stint.

24. An improved method of treating a tooth with an active agent as set forth in claim 22, wherein the step of introducing the active agent into the retaining material includes at least partially filling the internal region of the stint with the active agent to provide excess quantities of the active agent.

25. An improved method of treating a tooth with an active agent as set forth in claim 22, wherein the step of molding the stint to overlay the tooth includes molding the stint to overlay a plurality of teeth.

26. An improved method of treating a tooth with an active agent as set forth in claim 22, wherein the step of molding a stint from the stint material with the retaining material being formed adjacent to the internal region of the stint includes fusing the retaining material to the internal region of the stint.

27. An improved method of treating a tooth with an active bleaching agent, comprising the steps of:

making a model of the tooth;

positioning a retaining material between the model of the tooth and a stint material;

molding a stint from the stint material to define an internal region and an external region with the retaining material being formed adjacent to the internal region of the sting and to overlay the tooth and the adjacent gingiva tissue;

trimming the stint to overlay the tooth;

introducing the active bleaching agent comprising a solution of 11% perhydrol urea in a base solution of glycerine with a base stabilizer of 0.015% potassium citrate to brighten the tooth into the retaining material; and applying the stint containing the retaining material and the active agent upon the tooth.

28. An improved apparatus of treating a tooth embedded within a gingiva tissue with an active agent, comprising:

a stint having an internal region and an external region with the internal region of said stint defined for overlaying the tooth;

said stint terminating at the juncture of the tooth and the gingiva tissue;

a retaining material disposed within said internal region of said stint;

means for retaining said retaining material within said internal region of said stint;

said retaining material terminating at the termination of said stint proximate said juncture of the tooth and the gingiva tissue; and said retaining material at least partially sealing said internal region from said external region of said stint proximate said termination of said stint at the juncture of the tooth and the gingiva tissue when said stint is disposed upon the tooth for retaining the active agent therein enabling the active agent to be maintained in contact with the tooth when said stint containing said retaining material and the active agent is applied upon the tooth.

29. An improved apparatus of treating a tooth with an active agent as set forth in claim 28, wherein said stint comprises a molded sheet of plastic material.

30. An improved apparatus of treating a tooth with an active agent as set forth in claim 28, wherein said retaining material comprises a sheet of absorbent material.

31. An improved apparatus of treating a tooth with an active agent as set forth in claim 28, wherein said retaining material comprises a non-absorbent material.

32. An improved apparatus of treating a tooth with an active agent as set forth in claim 28, wherein said means for retaining said retaining material in said internal region of said stint includes friction means.

33. An improved apparatus of treating a tooth with an active agent as set forth in claim 28, wherein said means for retaining said retaining material in said internal region of said stint includes adhesive means.

34. An improved apparatus of treating a tooth with an active agent as set forth in claim 28, wherein said means for retaining said retaining material to said internal region of said stint includes heat fusing said retaining material to said stint.

35. An improved apparatus of treating a tooth with an active agent as set forth in claim 28, wherein said retaining material comprises a sheet of fibrous absorbent material.

36. An improved apparatus of treating a tooth with an active agent as set forth in claim 28, wherein said retaining material comprises a closed cell foam non-absorbent material.

37. An improved apparatus of treating a tooth with an active agent as set forth in claim 28, wherein said retaining material being disposed within said internal region of said stint includes preferentially inserting said retaining material into a selected portion of said internal region of said stint to preferentially treat a selected portion of the tooth adjacent said portion of said retaining material.

38. An improved apparatus of treating a tooth embedded within a gingiva tissue with an active bleaching agent, comprising:

a stint having an internal region and an external region with the internal region of said stint defined for overlaying the tooth;

said stint terminating at the juncture of the tooth and the gingiva tissue;

a retaining material disposed within said internal region of said stint;

means for retaining said retaining material within said internal region of said stint;

said retaining material terminating at the termination of said stint proximate said juncture of the tooth and the gingiva tissue;

said active bleaching agent comprising a solution of 11% perhydrol urea in a base solution of glycerine with a base stabilizer of 0.015% potassium citrate; and said retaining material retaining the active bleaching agent therein enabling the active bleaching agent to be maintained in contact with the tooth when said stint containing said retaining material and the active bleaching agent is applied upon the tooth.

* * * * *